United States Patent

Faust et al.

[11] Patent Number: 6,116,778
[45] Date of Patent: Sep. 12, 2000

[54] METHOD AND SYSTEM FOR QUANTITATIVE DETERMINATION OF SEAT CLIMATE ON SEAT CUSHIONS

[75] Inventors: Eberhard Faust, Stuttgart; Lothar Kassing, Nufringen; Karl Pfahler, Stuttgart; Markus Witzmann, Boeblingen, all of Germany

[73] Assignee: DaimlerChrysler AG, Stuttgart, Germany

[21] Appl. No.: 08/779,288

[22] Filed: Jan. 21, 1997

[30] Foreign Application Priority Data

Jan. 20, 1996 [DE] Germany .......................... 196 01 973

[51] Int. Cl.$^7$ .............................. G01K 3/00; G01N 17/00
[52] U.S. Cl. ........................................... 374/109; 73/865.6
[58] Field of Search ...................... 374/109, 141, 374/14; 73/73, 159, 432.1, 865.6, 865.9, 866, 38

[56] References Cited

U.S. PATENT DOCUMENTS 5,821,415  10/1998  Faust et al. ............................ 73/172
5,877,436   3/1999  Faust et al. ........................... 73/865.6
5,878,620   3/1999  Gilbert et al. ......................... 73/172

FOREIGN PATENT DOCUMENTS 2738913   3/1997  France ................................. 374/109
60-192976 10/1985 Japan .................................. 374/109

Primary Examiner—Hezron Williams
Assistant Examiner—Willie Morris Worth
Attorney, Agent, or Firm—Evenson, McKeown, Edwards & Lenahan, PLLC

[57] ABSTRACT

A method and a system for quantitative determination of the seat climate of a seat cushion is provided. For this purpose, the seat surface is subjected, during realistic mechanical loading of the seat cushion to be tested, to a flow of moisture from a climate mat. Any moisture stagnation at the seat surface is measured. For this purpose, the seat cushion, covered with a flexible multilayer climate mat, is loaded realistically via an anthropomorphically shaped seat testing punch. The climate mat consists of the following layers: a plurality of flat moisture sensors; a trouser material layer with low moisture uptake; a distribution layer that is readily permeable to air and has a noncompressible structure; a fleece layer that can be moistened and replaced as the moisture storage medium; an electrically insulating vapor barrier; and an electrically heatable heating mat that can be set to a specific temperature.

11 Claims, 1 Drawing Sheet

METHOD AND SYSTEM FOR QUANTITATIVE DETERMINATION OF SEAT CLIMATE ON SEAT CUSHIONS

BACKGROUND AND SUMMARY OF THE INVENTION

The invention relates to a method and a system for determining the seat climate on seat cushions.

In the development of seats, especially vehicle seats, the main issue is good sitting comfort because the occupants and especially the driver sometimes have to remain seated on vehicle seats for many hours with only limited movement. In this regard, questions of optimum seat pressure distribution and optimum seat climate play a role.

One very important criterion in the development of new vehicle seats or the evaluation of existing seats is their behavior regarding absorption of the moisture produced during prolonged sitting in the form of body perspiration. The climate behavior of a seat is determined by a number of factors, for example the material quality of the covering material, the nature and construction of the multi-layer combination of the covering material, the nature and form of the finishing of the seat covering, the material, nature, and structure of the seat foundation, and the like. If a seat cushion behaves poorly from the sitting climate standpoint, it cannot absorb the moisture given off by a person during prolonged sitting and conduct it into the environment. This produces a damp micro-climate between the person and the seat that is perceived as unpleasant.

In the course of seat development, various seat and cushion designs are prepared as trial samples and these must be compared with one another in an objective and reproducible fashion regarding various testing and evaluation criteria, especially as regards seat climate, in order to be able to pick the best trial sample in this way. Not only new trial samples from actual seat development but also various test seats from other sources, for example seats of earlier seat generations, used seats, or seats from outside development or manufacturing facilities, are compared with one another.

In the publication entitled SAE 1993 Transactions, Journal of Passenger Car, Section 6, Volume 102, pp. 136 to 141, an article by J. Temming was published entitled "A New Method to Assess the Summer Suitability of Car Seats." The article describes a method for spot measurement of the seat climate of vehicle seats. The middle of the seat surface is mechanically and uniformly loaded by a weight over a flat rectangular area of about 15×25 cm. The contact area of the test body can be heated to a human body temperature. By means of an interposed specifically moistened fleece, a certain amount of moisture can be added to the area in contact with the seat cushion. By heating this fleece to about 37° C., a specific moisture flow into the seat cushion is produced. By means of moisture sensors located in the contact zone, moisture stagnation on the seat surface can be determined and is intended to be a measure of the seat climate. The disadvantages of the known method include unrealistic sitting pressure distribution during climate measurement due to the cushion being loaded by a body that is rigid and flat in the contact zone. Another disadvantage is the limitation of measurement to a portion of the area located in the middle of the seat on the cushion; to a certain extent, only spot air conditioning is performed.

Experience with the measuring method according to the present invention has shown that the nature and area of cushion loading, and the type of cushion deformation, are very important parameters in the results of a seat climate measurement. With a pressure distribution that corresponds to the previously known measurement method, reproducible and especially informative, i.e. representative, seat climate measured values cannot be expected during measurement in and/or with limitation to a small partial area of the seat, according to experience with the invention. At best, only seats of the same kind can be compared as regards seat climate properties by using the known measurement method or the measured values obtained therewith, and then only with considerable limitations. Comparisons with measured climate values obtained using the known method for different kinds of seats cannot be compared with one another.

On the basis of this prior art, the goal of the present invention consists in further developing the measurement method and the measuring system for seat climate measurement in such fashion that the resultant measured values for seat climate are realistic, reproducible, and representative of the subjectively perceived seat climate for all possible test seats.

This goal is achieved according to the invention by a method for determining the seat climate of a seat cushion of a vehicle seat, in which the seat area is subjected to a moisture flow from a climate mat during realistic mechanical loading of the seat cushion to be tested. Any moisture stagnation at the seat surface is measured. The realistic loading of the seat surface of the seat cushion to be tested is accomplished with respect to total compressive force and sitting pressure distribution in the same way as when a person sits down, by means of an anthropomorphically simulated seat testing punch. The release of the moisture flow from the flexible climate mat interposed in the application area of the seat testing punch against the seat surface also takes place in the direction of the seat surface in such fashion that a quantity of moisture stored in the climate mat in a storage fleece, which is constant for each measurement, is slowly released into the seat surface by heating the climate mat approximately to body temperature.

A measuring system according to the invention is used to determine the seat climate of a seat cushion, especially for practicing the above-method. In the system, the seat cushion to be tested, received in a specific position in a testing machine and covered at the seat surface by a flexible climate mat, is loaded by means of a rigid seat testing punch that anthropomorphically and realistically simulates the area of the buttocks and thighs with regard to bones and soft parts in terms of the total compressive force and sitting pressure distribution as if a person were sitting down. The multilayer climate mat consists of a cover Layer, a storage fleece that stores moisture, a vapor barrier, and an adjustable heating mat, with the cover layer facing the seat cushion and the heating pad facing the seat testing punch during use. The climate mat is made openable between the cover layer and the vapor barrier and between the heating pad for replacement of the storage fleece. At least one flat moisture sensor with signal leads extending outward is located at an especially significant location between the seat surface and the climate mat.

According to the present invention, the seat surface, during a realistic mechanical loading of the seat cushion to be tested, is subjected to a small moisture flow from a climate mat corresponding to a natural sweating process, and any stagnation of moisture at the seat surface is measured.

The less the residual moisture, the better the seat cushion behaves in terms of seat climate. The seat surface of the seat cushion to be tested is loaded realistically in terms of total compressive force and sitting pressure distribution in the same way as when a person sits, using an anthropomorphically simulated seat testing punch. The required moisture flow from the flexible climate mat interposed in the application area of the seat test punch against the seat surface and facing the seat surface is produced by virtue of the fact that moisture is stored in a fleece in the climate mat and released as a result of heating approximately to body temperature.

The following advantages can be achieved by the present invention: (1) the tests proceed under precisely defined measurement conditions; (2) reproducible measurement results are obtained; (3) the measurement results from different seats can easily be compared with one another; (4) the measurements and/or tests can be conducted in a laboratory or in the test garage, i.e. it is not necessary to install the seat in the car; (5) test personnel are spared; (6) the measurement and/or testing of a seat itself requires only half the time in comparison with tests using test subjects; and (7) series measurements are possible without difficulty.

Other objects, advantages and novel features of the present invention will become apparent from the following detailed description of the invention when considered in conjunction with the accompanying drawings.

DETAILED DESCRIPTION OF THE DRAWINGS

Figure 1:
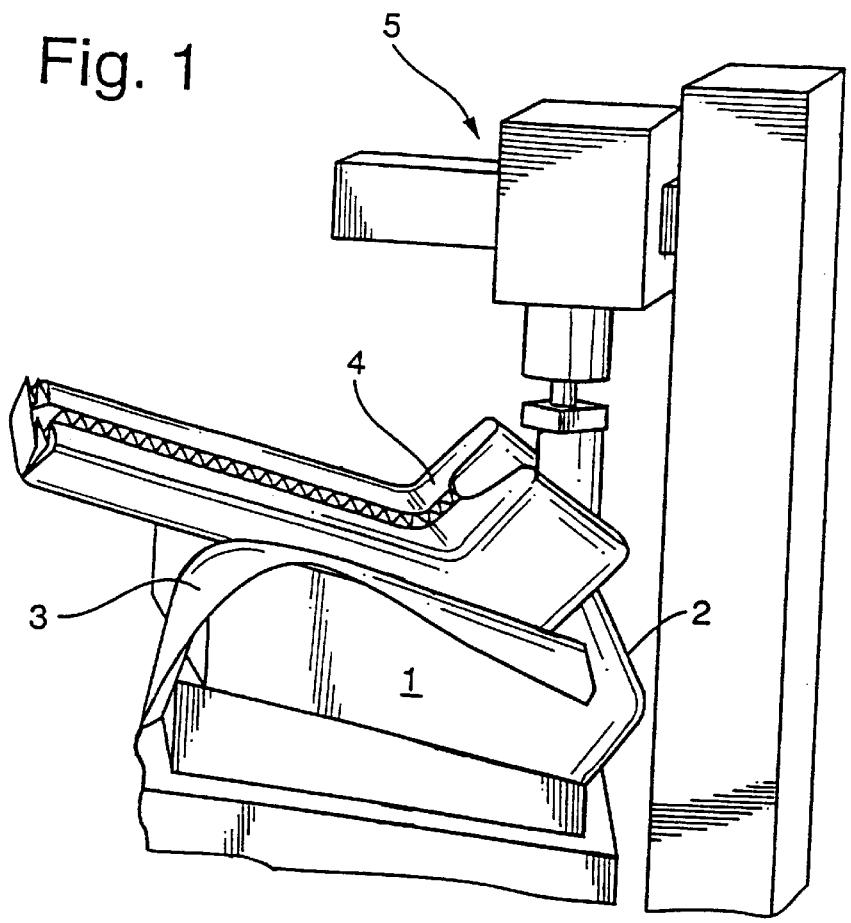
FIG. 1 shows a measurement system with a seat cushion to be tested in a testing machine, with a climate mat placed on a seat surface and an anthropomorphic seat testing punch placed on said mat according to the present invention.
Figure 2:
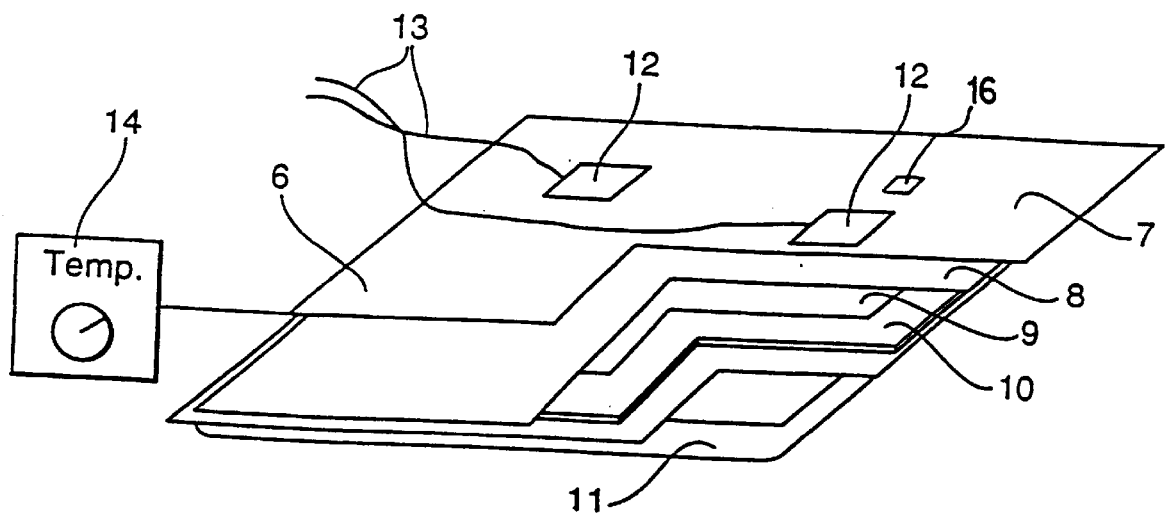
FIG. 2 shows a perspective open view of a climate mat as seen from the seat side according to the present invention.

The embodiment of a measuring system shown in FIG. 1 shows a testing machine 5 in which seat cushion 1 to be tested is received in a specific position. A climate mat 3 is placed on seat surface 2 of the cushion. The seat cushion is loaded by a seat testing punch 4 by which the sitting of a person on the seat cushion can be realistically simulated. As far as the rigid parts of the seat testing punch 4 are concerned, the latter simulates anthropomorphically these parts in terms of local distribution of thickness and softness, in the relevant areas of the pelvic and thigh areas, including the hip joints of a human skeleton, and with respect to the upholstery on this pressure element, the soft parts are simulated in the area of the buttocks, namely the muscle, connective, and fatty tissue. In particular, the area of the two ischial humps of the human buttocks and their immediate vicinity are simulated as naturally as possible by the seat testing punch as regards shape, position, hardness, and local hardness distribution. With such a seat testing punch, which is the subject of copending application Ser. No. 08/786,444, now U.S. Pat. No. 5,821,415 and entitled "SEAT TESTING PUNCH", filed on even date herewith, and commonly assigned to the assignee of the present invention, the specification of which is herein expressly incorporated by reference, the seat cushion can be loaded realistically as when a person sits down in terms of the total compressive force and sitting pressure distribution, which is an important prerequisite for an informative investigation of the seat cushion regarding its climate behavior.

To determine the seat climate of seat cushion 1, during such a realistic mechanical loading of seat surface 2, the latter is subjected to a moisture flow from a climate mat (3) and any moisture stagnation at the seat surface is measured. The moisture determined in the contact area between the climate mat 3 and the loaded seat surface 2 is measured and the moisture recorded as a measured value only after a steady state of mat temperature and moisture has established itself, which takes approximately ten minutes with the careful mat heating that is required. The moisture which is then measured is at least indirectly evaluated as a measure of the seat climate of the seat cushion in such fashion that high moisture values correspond to a poor seat climate and vice versa.

The release of a moisture current from interposed climate mat 3 in the direction of seat surface 2 is accomplished by virtue of the fact that in the climate mat, in a storage fleece 9, a quantity of moisture is stored that is constant for all measurements, and as a result of heating the climate mat approximately to body temperature, moisture is slowly released from the pad into seat area 2. Heating mat 11 is designed so that it is electrically heatable uniformly over its entire surface and can be adjusted precisely by regulator 14 to a certain presettable temperature. A temperature setpoint of about ±1° C. should be settable within a temperature range of 28 to 40° C.

Flexible multilayer climate mat 3 consists of a cover layer 6, itself composed of several layers, the above-mentioned storage fleece 9 that stores the moisture, a vapor barrier 10, and the above-mentioned adjustable heating pad 11. In the operating position, cover layer 6 faces seat cushion 1 and heating pad 11 faces seat testing punch 4.

For each individual measurement, storage fleece 9 must have a certain total moisture content and uniform moisture distribution within the storage fleece. It is also important to ensure that the storage fleece used has approximately the same properties as regards thickness, weight per unit area when dry, pore volume, fiber thickness, fiber material, and fiber surface quality so that the storage fleece 9 will have a constant moisture dispensing rate. Following frequent usage of storage fleeces and moistening with normal tap water, a certain calcification of the storage fleece can occur. A calcified storage fleece should not be used any longer.

To replace storage fleece 9, climate mat 3 can be opened both between cover layer 6 and vapor barrier 10 and between cover layer 6 and the heating pad 11, and reclosed in the correct position by rapid closures such as zippers or Velcro strips. The storage fleece, moistened uniformly and to a specific total moisture, is inserted without folding during replacement between the adjacent layers of the climate mat 3.

Cover layer 6 shown in the example of climate mat 3 is made, as mentioned above, in several layers and consists of a clothing layer 7 (such as trouser material) made of a yarn with a low moisture uptake ability and a distributing layer 8 of a fabric or knit that allows air to readily pass through and made of a yarn with a low moisture uptake ability and a structure that is not compressible or is only slightly compressible under the action of pressure, heat and moisture. Vapor barrier 10 shown as an example likewise consists of two layers of plastic films that are electrically insulating and do not allow moisture to pass through.

Between the seat surface and the climate mat, flat moisture sensors 12 that do not interfere with sitting are located at especially significant locations, with signal leads 13 extending outward. These leads are attached on the outside to cover layer 6 of climate mat 3. If there are several moisture sensors 12, they are advantageously located with some at points with a high sitting pressure and some at points with a low sitting pressure. It can also be advantageous to locate moisture sensors 12 pairwise and mirrorwise on climate mat 3 at points where the sitting pressure is approximately equal. At least one temperature sensor 16 can be integrated into the climate mat on the side facing the seat, with said temperature sensor advantageously being located at the position of a moisture sensor. The various moisture sensors 12 and temperature sensors 16 make it possible to determine during a seat climate measurement whether a steady state temperature and moisture state has established itself during the measurement process everywhere in seat surface 2 under load. The individual moisture values of different sensors 12 can either be computed to generate an average, especially when the various measured values differ only slightly. When there are pronounced differences in the locally measured moisture values, information about locally different distribution of seat climate conditions within the extent of the seat surface can also be obtained.

Repeated measurements of the seat climate conducted according to the invention on various seat cushions have shown that the measured moisture values can be reproduced very well. Moreover, comparisons of seat climate measurements and sample sitting by test subjects on different seats have shown that the measurements according to the invention are absolutely representative of subjective perceptions of seat climate.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for determining a seat climate of a seat cushion of a vehicle seat, the method comprising the steps of:

subjecting a seat area of the seat cushion to a moisture flow from a flexible climate mat during realistic mechanical loading of the seat cushion to be tested;

measuring any moisture stagnation at the seat area;

wherein said realistic mechanical loading of the seat cushion is performed using a rigid seat testing punch which anthropomorphically and realistically simulates a buttocks and thigh areas with regard to bones and soft parts of the human body in terms of a total compressive force and sitting pressure distribution when a person is sitting down; and wherein the subjecting of the seat area to a moisture is performed by releasing a moisture flow from the flexible climate mat interposed in an application area of the seat testing punch against the seat area, said release taking place in a direction of the seat surface in such fashion that a quantity of moisture stored in the flexible climate mat in a storage fleece is slowly released into the seat surface by heating the climate mat approximately to a human body temperature, said quantity of moisture being constant for each measurement performed.

2. A system for determining a seat climate of a seat cushion, the system comprising:

a test machine which receives the seat cushion to be tested;

a flexible climate mat which covers the seat cushion to be tested when arranged in the testing machine, said seat cushion being loaded via a rigid seat testing punch which anthropomorphically and realistically simulates a buttocks and thigh areas with regard to bones and soft parts of the human body in terms of a total compressive force and sitting pressure distribution when a person is sitting down;

wherein said flexible climate mat is a multilayer flexible climate mat comprised of a cover layer, a storage fleece which stores moisture, a vapor barrier, and an adjustable heating pad, said cover layer facing the seat cushion and said heating pad facing the seat testing punch during use;

wherein said multilayer flexible climate mat is openable between the cover layer and vapor barrier for replacement of the storage fleece and between the cover layer and the heating pad; and at least one flat moisture sensor having signal leads extending outward from the multilayer climate mat, said at least one moisture sensor being located at a predetermined location between the seat surface and the flexible climate mat.

3. The system according to claim 2, wherein said at least one moisture sensor is externally fastened to the cover layer of the flexible climate mat.

4. The system according to claim 2, wherein the cover layer comprises several layers, including a layer of clothing material made of a yarn having a low moisture uptake ability and a distribution layer composed of one of a fabric and knit which allows air to pass readily through and made of a yarn having a low moisture uptake ability and having a structure which is not compressible or only slightly compressible under an influence of pressure, heat, and moisture.

5. The system according to claim 2, wherein said vapor barrier comprises at least one layer of an electrically insulating plastic film that prevents moisture from passing therethrough.

6. The system according to claim 2, wherein a plurality of moisture sensors are applied to the flexible climate mat, said moisture sensors being located at locations having a high sitting pressure and at locations with a low sitting pressure.

7. The system according to claim 2, wherein a plurality of moisture sensors are mounted pairwise and mirrorwise on the flexible climate mat at points where sitting pressures are approximately the same.

8. The system according to claim 2, wherein at least one temperature sensor is integrated into the flexible climate mat on a side thereof facing the seat cushion.

9. The system according to claim 8, wherein the at least one temperature sensor is integrated into the flexible climate mat and is located at a position of one of said at least one moisture sensor.

10. The system according to claim 2, wherein the flexible climate mat is adjustable via said heating pad within a temperature range from 28 to 40° C. with respect to a temperature setpoint of ±1° C.

11. The system according to claim 2, wherein the flexible climate mat is divided in an area of the storage fleece, and wherein said cover layer, vapor barrier and heating pad are held together via rapid closure members.

* * * * *